(12) United States Patent
Levy

(10) Patent No.: US 11,185,671 B2
(45) Date of Patent: *Nov. 30, 2021

(54) APPARATUS AND PROCESS FOR PRODUCING $CO_2$ ENRICHED MEDICAL FOAM

(71) Applicant: Frank Levy, Fort Myers, FL (US)

(72) Inventor: Frank Levy, Fort Myers, FL (US)

( * ) Notice: Subject to any disclaimer, the term of this patent is extended or adjusted under 35 U.S.C. 154(b) by 79 days.

This patent is subject to a terminal disclaimer.

(21) Appl. No.: 16/418,434

(22) Filed: May 21, 2019

(65) Prior Publication Data

US 2019/0290893 A1 Sep. 26, 2019

Related U.S. Application Data

(63) Continuation of application No. 15/646,623, filed on Jul. 11, 2017, now Pat. No. 10,350,398, which is a continuation of application No. 14/509,459, filed on Oct. 8, 2014, now Pat. No. 9,744,342, which is a continuation of application No. 13/068,680, filed on
(Continued)

(51) Int. Cl.
*A61M 35/00* (2006.01)
*A61M 37/00* (2006.01)
*A61K 9/12* (2006.01)
*A61B 17/00* (2006.01)
*A01N 25/00* (2006.01)

(52) U.S. Cl.
CPC .......... *A61M 35/003* (2013.01); *A01N 25/00* (2013.01); *A61M 35/00* (2013.01); *A61M 37/00* (2013.01); *A61B 2017/00884* (2013.01); *A61B 2017/00893* (2013.01); *A61K 9/124* (2013.01)

(58) Field of Classification Search
CPC .... A61M 35/00; A61M 35/003; A61M 35/30; A61M 37/00; A61M 5/155; A61M 2005/006; A61M 11/02; A61B 2017/00884; A61B 2017/0893; A61B 2017/00893; A61K 9/12; A61K 9/122; A61K 9/124

See application file for complete search history.

(56) References Cited

U.S. PATENT DOCUMENTS

| 2,475,511 A | 7/1949 | Nicholson |
| 2,688,428 A | 9/1954 | Manhartsberger |

(Continued)

FOREIGN PATENT DOCUMENTS

| CN | 2179152 Y | 10/1994 |
| DE | 10161027 A1 | 6/2003 |

(Continued)

*Primary Examiner* — Emily L Schmidt
*Assistant Examiner* — Leah J Swanson
(74) *Attorney, Agent, or Firm* — Welsh Flaxman & Gitler LLC

(57) ABSTRACT

The present invention provides an apparatus for producing medical foam for wound care or hair stimulation. The apparatus includes a foam generation unit having a fluid reservoir, a fluid delivery line and a foam generation tip. The apparatus also includes a compressed gas unit having at least one container of compressed gas, a source of electric power, and a gas regulator valve. A supply of wound care or hair stimulating solution is communicably connected to the foam generation tip such that when the apparatus is operated medical foam is produced by the foam generator tip.

1 Claim, 5 Drawing Sheets

Related U.S. Application Data

May 17, 2011, now Pat. No. 8,876,749, which is a continuation-in-part of application No. 12/652,845, filed on Jan. 6, 2010, now abandoned, which is a continuation-in-part of application No. 12/210,368, filed on Sep. 15, 2008, now abandoned, which is a continuation-in-part of application No. 11/945,674, filed on Nov. 27, 2007, now Pat. No. 7,543,760.

(60) Provisional application No. 60/867,323, filed on Nov. 27, 2006.

(56) References Cited

U.S. PATENT DOCUMENTS

| | | | |
|---|---|---|---|
| 2,828,889 A | | 4/1958 | Joschko |
| 3,004,686 A | | 10/1961 | McKee |
| 3,034,332 A | | 5/1962 | Lederer |
| 3,831,844 A | | 8/1974 | Tropeano et al. |
| 3,879,703 A | | 4/1975 | Bonazoli et al. |
| 4,189,068 A | | 2/1980 | Apellaniz |
| 4,219,021 A | | 8/1980 | Fink |
| 4,744,356 A | | 5/1988 | Greenwood |
| 4,786,394 A | | 11/1988 | Enzer et al. |
| 4,950,230 A | | 8/1990 | Kendell |
| 5,135,026 A | | 8/1992 | Manska |
| 5,154,348 A | | 10/1992 | Ratnik et al. |
| 5,195,963 A | | 3/1993 | Yafuso et al. |
| 5,246,140 A | | 9/1993 | Thix et al. |
| 5,345,932 A | | 9/1994 | Yafuso et al. |
| 5,395,318 A | | 3/1995 | Kaprelian |
| 5,580,530 A | | 12/1996 | Kowatsch et al. |
| 5,699,961 A | | 12/1997 | Ratnik et al. |
| 5,875,776 A | * | 3/1999 | Vaghefi ............. A61M 15/0045 128/203.15 |
| 5,964,223 A | | 10/1999 | Baran |
| 6,164,556 A | | 12/2000 | Dupre et al. |
| 6,192,883 B1 | | 2/2001 | Miller, Jr. |
| 6,295,007 B1 | | 9/2001 | O'Meara |
| 6,315,762 B1 | | 11/2001 | Recinella et al. |
| 6,378,570 B1 | | 4/2002 | Shipachev et al. |
| 6,402,047 B1 | | 6/2002 | Thomas |
| 6,474,091 B2 | | 11/2002 | Guerra |
| 6,572,873 B1 | | 6/2003 | Osman et al. |
| 6,959,708 B1 | * | 11/2005 | Rasor .................... A61K 31/21 128/203.12 |
| 7,543,760 B2 | | 6/2009 | Levy et al. |
| 8,876,749 B2 | | 11/2014 | Levy |
| 9,744,342 B2 | | 8/2017 | Levy |
| 10,155,093 B2 | | 12/2018 | Levy et al. |
| 10,322,271 B2 | | 6/2019 | Levy et al. |
| 10,350,398 B2 | | 7/2019 | Levy |
| 10,350,399 B2 | | 7/2019 | Levy et al. |
| 2001/0044618 A1 | | 11/2001 | Recinella et al. |
| 2002/0017328 A1 | | 2/2002 | Loo |
| 2002/0174578 A1 | | 11/2002 | Ross |
| 2003/0181850 A1 | | 9/2003 | Diamond et al. |
| 2005/0000981 A1 | | 1/2005 | Peng et al. |
| 2005/0092315 A1 | | 5/2005 | Bachelder |
| 2005/0103342 A1 | | 5/2005 | Jorczak et al. |
| 2005/0119607 A1 | | 6/2005 | Van Der Linden et al. |
| 2006/0004322 A1 | | 1/2006 | Uesugi et al. |
| 2006/0071091 A1 | | 4/2006 | Ratnik |
| 2006/0074386 A1 | | 4/2006 | Wollmann |
| 2006/0178620 A1 | | 8/2006 | Wollmann et al. |
| 2007/0104616 A1 | | 5/2007 | Keenan et al. |
| 2007/0104651 A1 | | 5/2007 | Wright et al. |
| 2007/0111298 A1 | | 5/2007 | Muller et al. |
| 2007/0244429 A1 | | 10/2007 | Nguyen et al. |
| 2008/0004549 A1 | | 1/2008 | Anderson et al. |
| 2008/0120992 A1 | | 5/2008 | Levy et al. |
| 2008/0167621 A1 | | 7/2008 | Wagner et al. |
| 2009/0062741 A1 | | 3/2009 | Smith et al. |
| 2009/0318890 A1 | | 12/2009 | Levy |
| 2010/0101579 A1 | | 4/2010 | Levy |
| 2011/0112041 A1 | | 5/2011 | Schiffmann |
| 2011/0218411 A1 | | 9/2011 | Keenan et al. |

FOREIGN PATENT DOCUMENTS

| | | | |
|---|---|---|---|
| EP | 2468204 A1 | 6/2012 | |
| WO | WO-9300951 A1 * | 1/1993 | ........ A61M 15/0066 |
| WO | 0072821 A1 | 12/2000 | |
| WO | 0241872 A1 | 5/2002 | |
| WO | 2005048984 A1 | 6/2005 | |

* cited by examiner

APPARATUS AND PROCESS FOR PRODUCING CO$_2$ ENRICHED MEDICAL FOAM

RELATED APPLICATIONS

This application is a continuation of U.S. patent application Ser. No. 15/646,623, filed Jul. 11, 2017, which is a continuation of U.S. patent application Ser. No. 14/509,459 filed Oct. 8, 2014, which issued as U.S. Pat. No. 9,744,342, which is a continuation of U.S. patent application Ser. No. 13/068,680 filed May 17, 2011, which issued as U.S. Pat. No. 8,876,749, which is a continuation in part of U.S. patent application Ser. No. 12/652,845 filed Jan. 6, 2010, which is abandoned, which is a continuation-in-part of U.S. patent application Ser. No. 12/210,368 filed Sep. 15, 2008, which is abandoned, which is continuation-in-part of U.S. patent application Ser. No. 11/945,674 filed Nov. 27, 2007, which issued as U.S. Pat. No. 7,543,760, which claims the benefit of U.S. Provisional Patent Application Ser. No. 60/867,323 filed Nov. 27, 2006, the disclosures of which are incorporated herein by reference in their entirety.

FIELD OF THE INVENTION

This invention relates to an apparatus and process for producing CO$_2$ enriched medical foam for use in wound care and hair growth stimulation.

BACKGROUND OF THE INVENTION

The present invention utilizes the Venturi effect to produce medical grade foam comprising CO$_2$ for use in applications such as wound care and hair growth stimulation. The apparatus of the present invention is simple to manufacture and use because it does not require an impeller and incorporated fan with a foam generator in order to create and dispense the foam.

The Venturi effect is an example of Bernoulli's principle, in the case of incompressible fluid flow through a tube or pipe with a constriction in it. The fluid velocity must increase through the constriction to satisfy the equation of continuity, while its pressure must decrease due to conservation of energy: the gain in kinetic energy is supplied by a drop in pressure or a pressure gradient force.

The limiting case of the Venturi effect is choked flow, in which a constriction in a pipe or channel limits the total flow rate through the channel because the pressure cannot drop below zero in the constriction. Choked flow is used to control the delivery rate of water and other fluids through spigots and other types of valves. The portable apparatus of the present invention utilizes a source of compressed gas, namely CO$_2$, to produce the desired pressure and airflow for the effective creation of medical foam, which foam is, in turn, used for wound care and hair growth stimulation. To date, medical foam has been used strictly in sclerosing applications, wherein blood vessels are destroyed. Medical foam has not been previously utilized in wound therapy or hair growth techniques wherein cell growth is encouraged. CO$_2$ enriched foam has certainly not been put to such uses.

SUMMARY OF THE INVENTION

The present invention provides for a novel apparatus for producing medical foam as well as a process for utilizing such foam in wound care and hair growth applications. One embodiment in the present invention features an apparatus for producing medical foam comprising (i) a foam generation unit having a fluid reservoir, a fluid delivery line and a foam generation tip; and (ii) a compressed gas unit having at least one container of compressed gas, a source of electric power and the gas regulator valve.

The fluid reservoir contains a medical solution for producing the foam. The compressed gas is any suitable compressed gas. Suitable compressed gases may preferably include carbon dioxide, atmospheric air, helium, or mixtures thereof. The compressed gas is contained in one or more compressed gas containers. The apparatus has a source of electric power that may be delivered by batteries providing between about 3-24 volts. The apparatus also has a foam generation tip that includes a membrane providing a surface for the formation of medial foam. In a preferred embodiment, the gas regulator valve is an electronically activated solenoid. Additionally preferred, the gas regulator valve is an electronically activated solenoid controlled by a pressure activation switch or actuator. The pressure switch activates the solenoid when depressed.

In one embodiment, the present invention utilizes an air delivery system whereby the air is delivered by compressed gas. Any compressed gas can be used. Preferably, the compressed gas is selected from compressed ambient air, carbon dioxide, helium, oxygen, or combinations thereof. Carbon dioxide is especially preferred for using the medical foam produced by the apparatus in wound treatment and hair growth stimulation.

In another embodiment, the apparatus of the present invention includes compressed air storage, with a hose or other acceptable transport mechanism to deliver the compressed gas to the foam generation tip or any other receptacle. The foam generation tip includes a novel arrangement by which compressed air enters a first end of the foam generation tip through an air inlet. The resultant pressure produced within the foam generation tip draws medical solution into the interior of the tip through a second inlet. The compressed air continues to travel towards the second end of the foam generation tip onto which a membrane is affixed. The membrane provides a surface at which the medical solution mixes with the compressed air and the medical solution foams. The compressed air passes through the membrane and lifts the foams off the membrane outward from the foam generation tip. Thus, the solution, now foamed by the compressed gas, can be delivered and applied to a wound or area of the body where hair growth is desired.

In another embodiment, a user will utilize two separate units of the apparatus wherein a first unit includes at least one compressed air cylinder and a valve for controlling the release of compressed air from the cylinder. In one embodiment, the valve for controlling the release of compressed air is an electronic solenoid.

The present invention also relates to methods of medical treatment. In one embodiment the invention is a method for providing CO$_2$ enriched foam and applying such foam to a wound comprising the steps of: (i) providing a portable CO$_2$ apparatus, (ii) providing a container with a medical solution, the container having an entrance, an exit and a release means regulating the exit; (iii) attaching a medically acceptable directional device from the apparatus to the entrance of the container; (iv) initiating an actuator of the apparatus to release CO$_2$; (v) activating the release means to produce a medical foam containing CO$_2$; and (vi) applying the medical foam to a wound to attract oxygen to the wound and thereby promote healing. In medical uses, CO$_2$ is used because it is safer and has less complications than air or oxygen in the same uses. CO$_2$ diffuses more naturally in body tissues and is absorbed in the body more rapidly and with less side effects. Medical foam produced in this manner may alternatively be applied to a skin surface of the human body to stimulate hair growth.

In a preferred embodiment, the $CO_2$ gas that is expelled from the apparatus will ultimately be used for foaming of medical solutions to produce a $CO_2$ enriched foam for the healing of ulcerations. These solutions may include, but would not be limited to saline, aloe, Amerigel®, microbial agents, and surfactants. $CO_2$ is used to aerate the solution and subsequently produce a medical foam for particular use in the field of wound and ulceration treatment. $CO_2$ enriched foam with the addition of medically appropriate solutions and surfactants will aid in the debridement of a wound, as well as, more efficient and more rapid healing of the affected area by drawing oxygen to that area.

The apparatus used in the present invention is portable, compact, and electronic, which makes it convenient for various portable medical uses including military field use. The apparatus is also well suited for any other use requiring $CO_2$ for its performance, such as compartmentalization, aid in ulcer healing, and aid in increasing follicle hair stimulation to promote hair growth. The apparatus of the present invention can also be adapted for dispensing other gases under the same nature, such as oxygen, helium, or any other gas needed to be contained in a compact, portable delivery system. In a preferred embodiment, the present invention is completely battery operated.

The invention can be used to provide $CO_2$ or like gases to one syringe, two syringes with a stopcock connector, or any container that can house or store the $CO_2$ before using it to aid in ulcer healing, and/or in increased follicle hair stimulation to aid in hair growth.

The invention can deliver $CO_2$ from an adjustable port that controls the psi from 0 psi to 120 psi.

Previous methods utilizing large $CO_2$ tanks and regulators are dangerous because of the risk of a seal, valve, or part malfunction causing a projectile in a medical setting. The present invention is safer as it eliminates this possibility of malfunction.

The invention requires very little space to store, as opposed to the cumbersome existing tank systems and is much easier to use, with a push button actuator to initiate operation. The present invention is much less expensive than current $CO_2$ tank systems.

Acquisition of the $CO_2$ in the present invention now requires only cartridges which can be delivered in a small box. The current tanks require filling at a filling station which involves the transport of a large quantity of $CO_2$ which could also result in an explosion in the event of a motor vehicle crash.

DETAILED DESCRIPTION OF PREFERRED EMBODIMENTS

Other objects, features and advantages will occur from the following description of a preferred embodiment and the accompanying drawings, in which.

Figure 1:
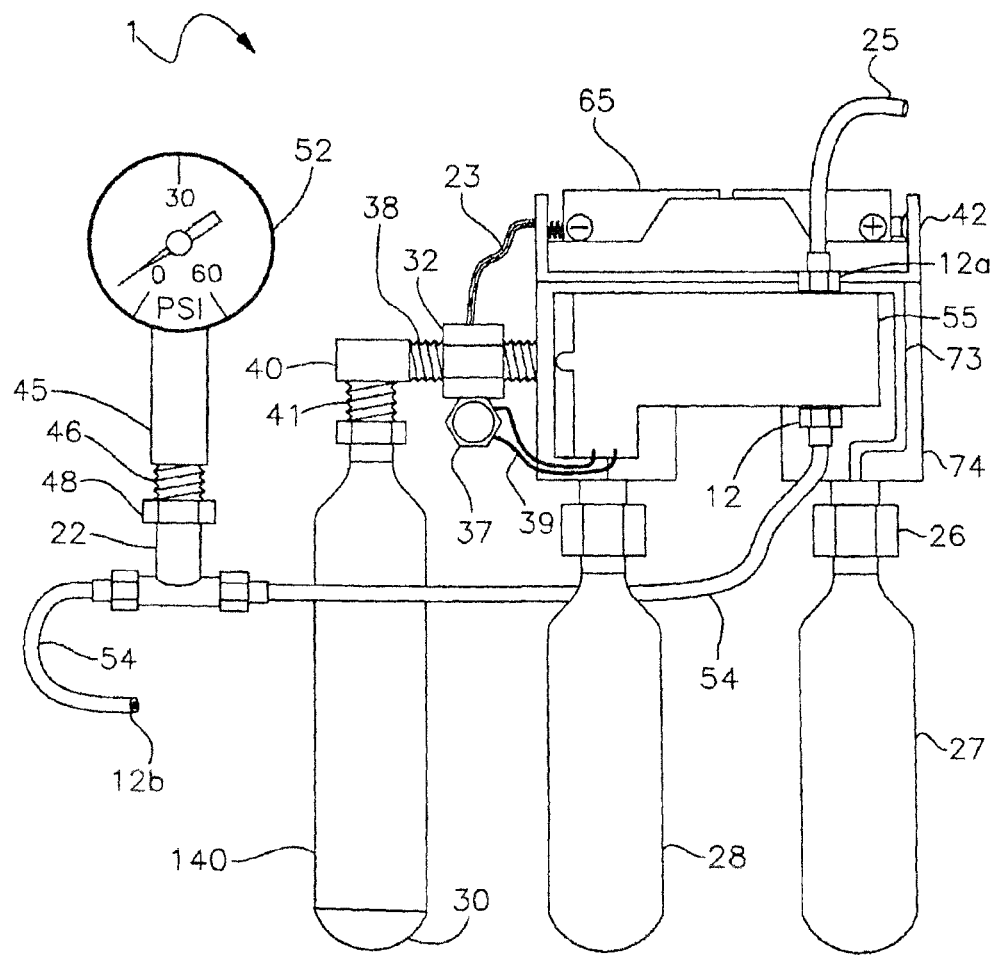
FIG. 1 is a side perspective and partly schematic view of an apparatus including compressed gas ($CO_2$) cylinders and a solenoid of the present invention.

In FIG. 1 compressed gas unit 1 comprises solenoid 55 with at least one compressed gas ($CO_2$) cylinder 27. In one embodiment, compressed gas cylinder 27 is 25 g or larger. Compressed gas cylinder 27 is secured into position to unit 1 by means of cylinder cartridge puncture valve 26 and a fitting 74. In a preferred embodiment, cylinder cartridge puncture valve 26 has a mechanism for piercing cylinder 27, as is known, and holding or securing said cylinder in place. Compressed air is delivered to solenoid 55 from compressed gas cylinder 27 through cylinder cartridge puncture valve 26 and a channel 73 of fitting 74. Compressed gas unit 1 has at least one battery 65, held in place by battery holder 42, for providing electrical power by which solenoid 55 may be activated and then regulated by a pressure activation switch or actuator 37. Battery 65 supplies power to solenoid 55 through switch wire assembly 23, which is connected to activation switch 37. This switch is mounted to a pressure nut 32 carried on threaded conduit 38. Compressed air unit 1 has electrical wiring 39 for providing necessary electricity from switch 37 to solenoid 55. Unit 1 also comprises a black rock regulator 140, which is controlled by secondary regulator adjustment knob 30 when solenoid 55 is activated. Black rock regulator 140 is communicably connected to unit 1 by an elbow pipe 40. The elbow pipe includes a threaded vertical conduit segment 41 joined to regulator 140 through a connector nut and a threaded horizontal conduit 38, which is engaged by pressure nut 32.

Compressed gas cylinder 27 is secured to unit 1 by cartridge puncture valve 26 as is commonly known. In one embodiment, compressed gas cylinder 27 is a 25 g cylinder. Compressed air leaves black rock regulator 140 through a 10/32" hose port 12b and flows through a hose junction 22, by means of ⅛" pressure hose 54, until reaching the 10/32" hose port 12 affixed to solenoid 55. From hose port 12, the compressed air enters solenoid 55. Compressed air unit 1 also has an outlet air port 25, which is connected to solenoid 55 through intermediate 10/32" hose port 12a for transporting compressed gas, namely $CO_2$, from solenoid 55 in compressed gas unit 1 to foam generation unit 2, FIG. whenever the solenoid is opened. Outlet gas may be monitored with pressure gauge 52 connected to hose junction 22 through a conduit 45 having threads 46. The threaded end of conduit 45 interengages a nut 48 carried by hose junction 22.

In certain embodiments a second compressed gas cylinder 28, featuring a 12 g or 16 g compressed gas cylinder, may be used in addition to or in lieu of gas cylinder 27. In still other embodiments a larger compressed gas cylinder and expansion chamber may be substituted for the gas cartridges previously described in accordance with the invention. The size and number of compressed gas containers are not limitations of the invention.

Figure 2:
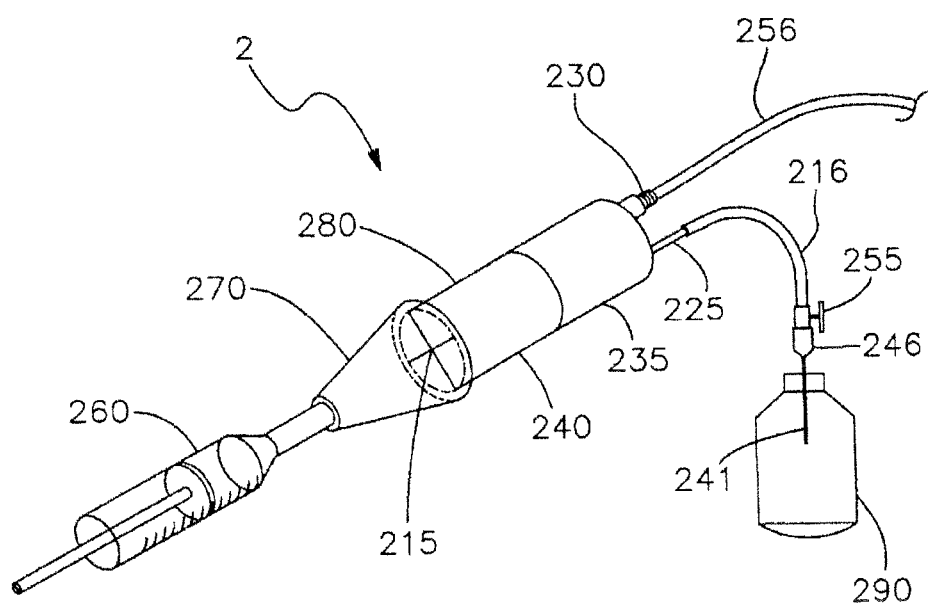
FIG. 2 is a perspective view of the foam generating tip and medical solution reservoir.

In FIG. 2, a $CO_2$ enriched foam generating unit 2 features a micro hose 256 for receiving compressed gas from unit 1. Compressed $CO_2$ leaving unit 1 via outlet air port 25 enters unit 2 via micro hose 256. Compressed gas passes through air hose inlet 230 and enters a foam generation tip 280.

Figure 3:
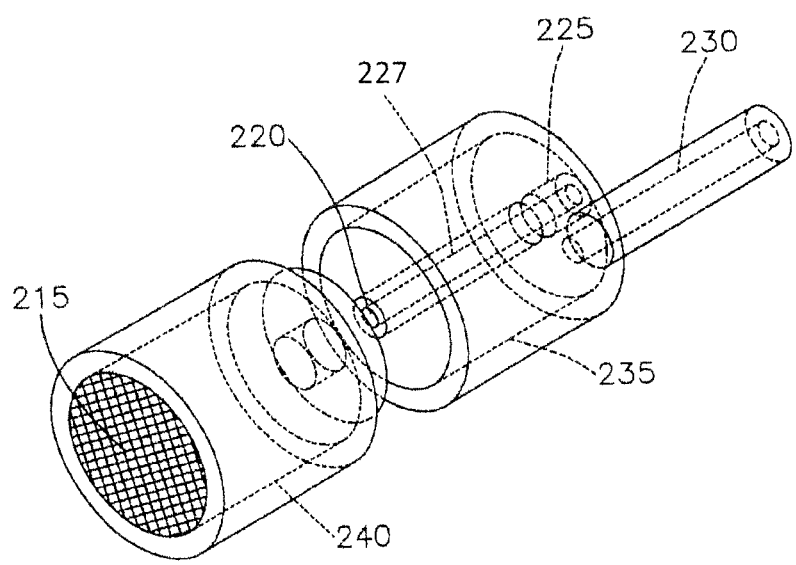
FIG. 3 is a close-up view of the foam generating tip shown in FIG. 2.

As shown in FIG. 3 foam generation tip 280 also includes foam solution delivery line 227 that has an outlet 220 for delivering foam solution into upper chamber 240. This solution may include any of various solutions such as, but not limited to various wound wash solutions, saline, aloe, microbial agents and surfactants which are appropriate for treating wounds and ulcerations. For example, Amerigel® solution may be effectively utilized as the foam solution. Solutions for stimulating hair growth include monoxidil marketed under the brand name Rogaine®. In a preferred embodiment, medical solution from solution reservoir 290, FIG. 2, travels up needle 241 and hub 246 when compressed gas enters tip assembly 280 through inlet 230 after being actuated and released from unit 1. Compressed gas entering tip assembly 280 imparts negative pressure on solution in reservoir 290 and draws solution through needle 241 and into tip solution inlet 225 (FIGS. 2 and 3) through hose 216 due to the Venturi effect. Stopcock 255 is used to regulate or stop flow of solution from reservoir 290. Solution enters solution delivery line 227 from solution line 216. Compressed gas traveling from lower chamber 235 to upper chamber 240 creates negative pressure inside the foam generation tip 280, such that medical foam solution exiting outlet 220 mixes with compressed $CO_2$ and forms $CO_2$ enriched medical foam that forms on membrane 215. The force of the compressed gas traveling through foam generation tip 280 and exiting through membrane 215 lifts medical foam/foams outward from membrane 215 and projects the foam into the foam dispensing port 270. The medical foam then exits tip assembly 280 through syringe hub 260 and is directed onto a wound or ulceration requiring treatment. Specifically, $CO_2$ enriched foam may be applied directly to a wound or ulceration. The $CO_2$ attracts oxygen to the wound/ulceration, which promotes healing. This is an unexpected beneficial result as, to date, the use of medical foams has been largely limited to sclerotherapy wherein blood vessels/tissue are destroyed. $CO_2$ enriched foam produced in the foregoing manner may alternatively be used to stimulate hair follicle growth.

Figure 4:
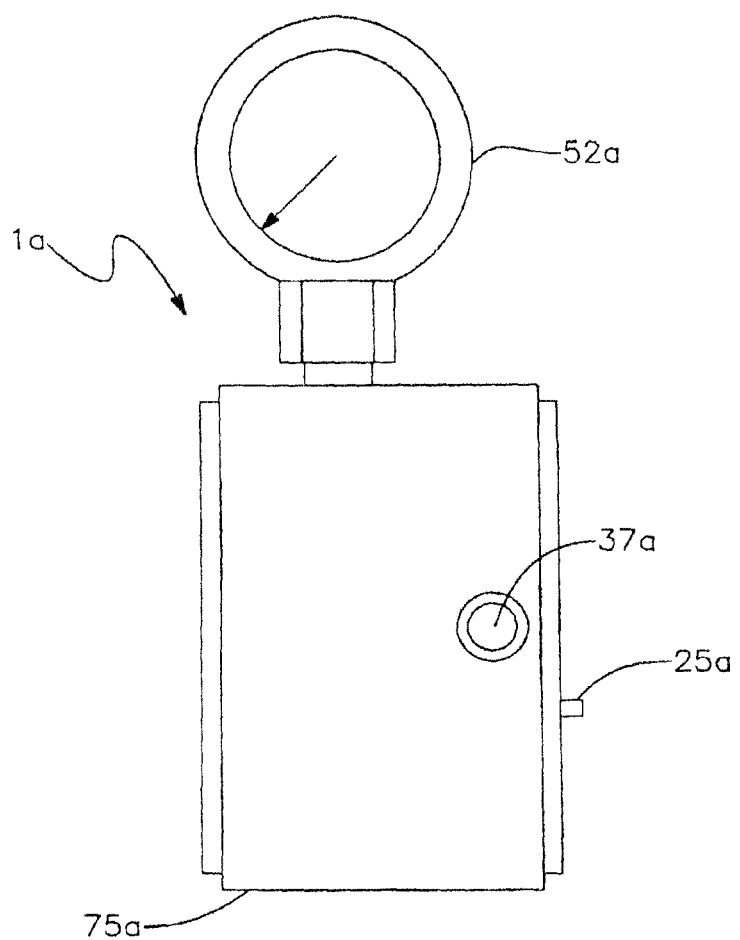
FIG. 4 is a schematic front view of an alternative compressed gas unit enclosed in a housing.
Figure 5:
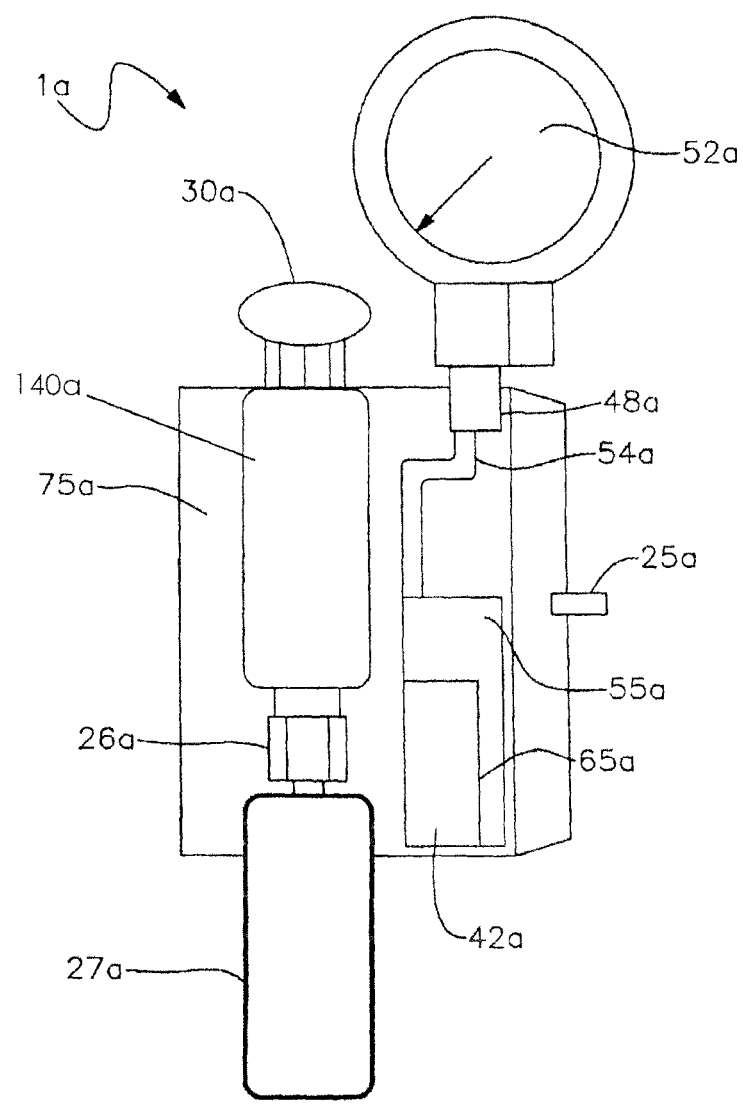
FIG. 5 depicts a schematic layout of the components of the compressed gas unit of FIG. 4.

FIGS. 4 and 5 depict an alternative embodiment of a compressed gas unit 1a wherein various components of the gas unit are enclosed in a housing 75a. The components of unit 1a are designated by reference numerals that correspond to those of the previously described embodiment and further include "a" designations. In particular, a $CO_2$ cartridge 27a is connected by a puncture valve 26a to a regulator 140a. The regulator is controlled by an adjustment knob 30a. Regulator 140a is connected through a conduit 54a to both a pressure gauge 52a and a solenoid 55a. More particularly, gauge 52a is connected to a coupling 48a. Solenoid 55a is powered by a battery 65a, which is itself held in place within the housing 75a by a holder 42a. A user accessible luer fitting 25a is communicably connected to solenoid 55a and extends exteriorly of housing 75a.

Unit 1a is activated to open solenoid 55a by engaging switch 37a. The compressed gas unit operates in a manner analogous to that previously described to provide compressed $CO_2$ from cartridge 27a through luer fitting 25a to an attached foam generating tip as depicted in FIGS. 2 and 3.

From the foregoing it may be seen that the apparatus and method of this invention provides for a novel and beneficial means for wound care and hair growth treatment. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

Other embodiments will occur to those skilled in the art and are within the following claims:

What is claimed is:

1. A method of making a $CO_2$ enriched medical therapy solution comprising the steps of: providing a portable compressed $CO_2$ unit adapted for selective attachment of a compressed gas cylinder containing compressed $CO_2$ thereto; selectively securing the compressed gas cylinder containing compressed $CO_2$ to the compressed $CO_2$ unit; providing a reservoir with a medical therapy solution; communicably interconnecting the reservoir with the compressed $CO_2$ unit; initiating the compressed $CO_2$ unit to deliver compressed $CO_2$ from the compressed gas cylinder and draw the medical therapy solution from the reservoir to generate a $CO_2$ enriched medical therapy solution; and forcing the compressed $CO_2$ from the compressed gas cylinder through a membrane to lift the $CO_2$ enriched medical therapy solution outward from the membrane and project the $CO_2$ enriched medical therapy solution for treatment.

\* \* \* \* \*